United States Patent [19] [11] Patent Number: 4,900,315
Lundqvist et al. [45] Date of Patent: Feb. 13, 1990

[54] DISPOSABLE APPLICATOR

[76] Inventors: Mona K. Lundqvist, Brandsberga, Pl. 223, S-26070 Ljungbyhed; Bengt E. Malmborg, Skånegatan 47, S-252 52 Helsingborg, both of Sweden

[21] Appl. No.: 332,446

[22] Filed: Mar. 31, 1989

Related U.S. Application Data

[63] Continuation of Ser. No. 169,153, Mar. 8, 1988, abandoned, which is a continuation of Ser. No. 873,399, Jun. 12, 1986, abandoned.

[30] Foreign Application Priority Data

Jun. 13, 1985 [SE] Sweden ................. 8502933

[51] Int. Cl.4 ............................................ A61M 35/00
[52] U.S. Cl. ...................................... 604/311; 604/15
[58] Field of Search ............... 604/3, 15, 18, 72, 73, 604/181, 187, 193, 194, 218, 220, 223, 233, 310, 311, 11; 222/541; 264/157, 159, 242, 267

[56] References Cited

U.S. PATENT DOCUMENTS

| 2,059,966 | 11/1936 | Kaufman et al. | 604/200 |
| 2,747,574 | 5/1956 | Lorenzo | 604/200 |
| 3,043,304 | 7/1962 | Higgins | 604/233 |
| 3,506,008 | 4/1970 | Huck | 604/193 |
| 3,642,000 | 2/1972 | Baker | 604/193 |
| 3,703,765 | 11/1972 | Perez | 222/541 |
| 3,737,501 | 6/1973 | Dunipace | 264/159 |
| 4,240,421 | 12/1980 | Carr | 604/187 |
| 4,248,227 | 2/1981 | Thomas | 222/541 |
| 4,645,488 | 2/1987 | Matukas | 604/218 |

FOREIGN PATENT DOCUMENTS

| 134308 | 10/1972 | Denmark . | |
| 0006545 | 6/1979 | European Pat. Off. . | |
| 0848081 | 9/1952 | Fed. Rep. of Germany | 604/193 |
| 1914754 | 3/1969 | Fed. Rep. of Germany . | |
| 2653051 | 11/1976 | Fed. Rep. of Germany . | |
| 0274619 | 7/1951 | Switzerland | 604/193 |

Primary Examiner—C. Fred Rosenbaum
Assistant Examiner—Sharon Rose
Attorney, Agent, or Firm—Pravel, Gambrell, Hewitt, Kimball & Krieger

[57] ABSTRACT

This invention concerns a disposable single dose syringe type applicator in the form of an elongated body that comprises two integrally joined sections which can be separated by breaking. One section is a tubular barrel section which constitutes a medicament reservoir having two openings. The other section is a rod-like section, which constitutes a plunger, which, by reason of being integrally joined to the barrel section seals one opening of the reservoir. The reservoir section is prefilled with a medicament. At the other opening end of the medicament reservoir, through which it is prefilled with medicament, there is arranged an easily removable sealing means. After separation, the plunger section slidably fits into the reservoir in such a way that essentially the whole medicament content of the reservoir is ejected therefrom when the plunger is inserted into the reservoir.

20 Claims, 3 Drawing Sheets

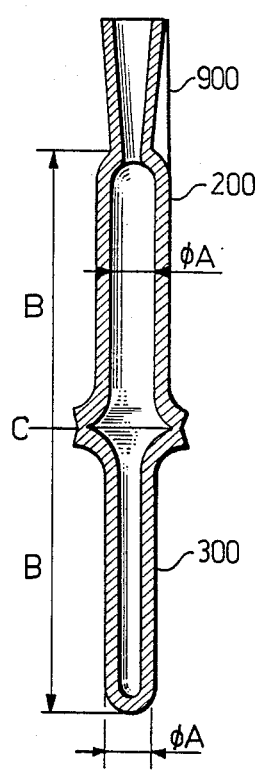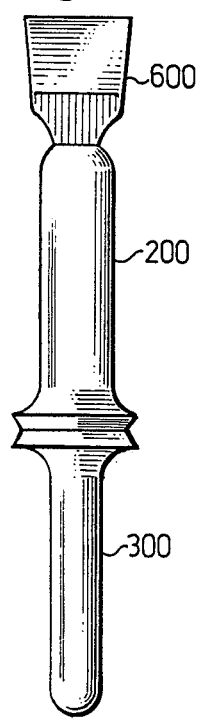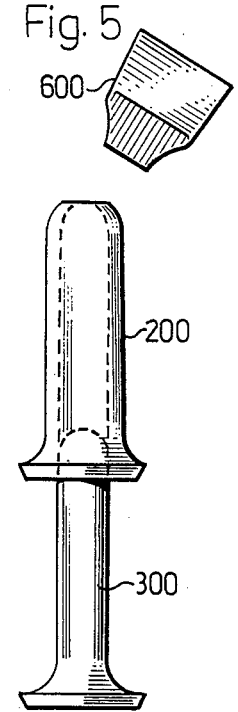

DISPOSABLE APPLICATOR

This is a continuation of co-pending application Ser. No. 169,153 filed on Mar. 8, 1988, now abandoned, which is a continuation of co-pending application Ser. No. 873,399 filed on June 12, 1986, now abandoned.

BACKGROUND OF THE INVENTION

For many medical reasons it is necessary or desirable to administer various medicaments to body cavities. In order to provide a simple method of applying the medicament with a minimum of discomfort, the medicaments are often administered with a syringe type applicator. A patient may self administer the medication by use of a syringe prefilled with the prescribed medicament at the desired dosage level.

An applicator of this type is disclosed in European Patent Application No. 6545. This applicator consists of an expandable cannula provided with a longitudinal cylindrical hollow chamber. The chamber contains a metered quantity of a substance to be administered to a patient. Both ends of the chamber are provided with easily removable sealing means. A rod provided with a grip at one end and with a piston conveniently fitting the hollow chamber of the cannula at the other end is arranged such that by pushing the rod into the hollow chamber all the substance contained therein is ejected. This syringe type applicator is intended for single use and has a relatively simple form. However, it is comprised of several parts which complicates its process of manufacture. Manufacturing costs of disposable applicators are of critical importance for such devices. The applicator disclosed by European Pat. No. 6545 would be undesirably expensive to manufacture.

A conventionally used applicator for administering medicaments into body cavities is disclosed in Danish Pat. No. 134,308. This applicator comprises a flat container section and a metering chamber, in the form of a cannula, which can be inserted into, e.g. the nostril. When pressure is applied to the container section the drug is ejected through the cannula. The pressure is applied by the fingers of the user.

The type of applicator disclosed by Danish Pat. No. 134,308 has been well accepted and works well in many cases. A general problem with it is, however, dosing accuracy. In order to obtain dosing accuracy, which is of critical importance for some types of drugs, the drug composition included in the container must have low viscosity. In order to obtain approximately the correct dose of high viscosity compositions, a large excess of the drug composition must be filled into the container. It is, however, generally not accepted by the health authorities that single dose containers have more than a slight excess of the active drug.

The ideal situation to be achieved in a disposable applicator is, of course, that it should contain only a single dose which corresponds exactly in amount to the dose that shall be administered. It is thus obvious that the type of applicator disclosed by Danish Pat. No. 134,308 is not well suited to administering high viscosity composition. When low viscosity compositions are administered through an applicator of this type, the problems are less, but even then are not totally avoided.

This invention provides a disposable single dose of the Invention syringe type applicator for applying medicaments to body cavities.

The disposable single dose syringe type applicator of the present invention is an elongated body which comprises two integrally joined sections which can be separated by breaking. One is a barrel, a hollow tubular section, which constitutes a medicament reservoir having two openings. The other section is a plunger which, prior to separation from the medicament reservoir section, seals one opening of the reservoir. The reservoir is filled with medicament from the other opening end thereof after which such opening end of the medicament reservoir is provided with an easily removable sealing means. After separation, the rod-like plunger section slidably fits into the barrel, or reservoir, in such a way that essentially the whole medicament content of the reservoir is ejected therefrom when the plunger is inserted into the reservoir.

The syringe applicator of this invention can be easily and inexpensively manufactured in one piece. The disclosed applicator has a high dosing accuracy and can be used for various types of medicament compositions. The applicator of the invention delivers essentially the whole amount of medicament with which it is prefilled.

BRIEF DESCRIPTION OF THE DRAWINGS

FIG. 3 is a sectional view of another embodiment of an applicator according to the invention.

FIG. 4 is a plan view of the applicator of FIG. 3.

FIG. 5 is a plan view of the applicator of FIG. 4 in the ready to use state.

DETAILED DESCRIPTION OF THE PREFERRED EMBODIMENT

A characterizing feature of an applicator according to the present invention is that the tubular section or barrel which serves as the medicament reservoir and the second rod-like section which serves as the plunger are manufactured in one piece as a unitary body. When the applicator is used the barrel section constituting the medicament reservoir and the second rod-like section constituting the plunger are separated by breaking the integral joint there between. In this context the term "breaking" includes all ways of taking apart the two integrally joined sections, such as cracking, turning etc.

Figure 1:
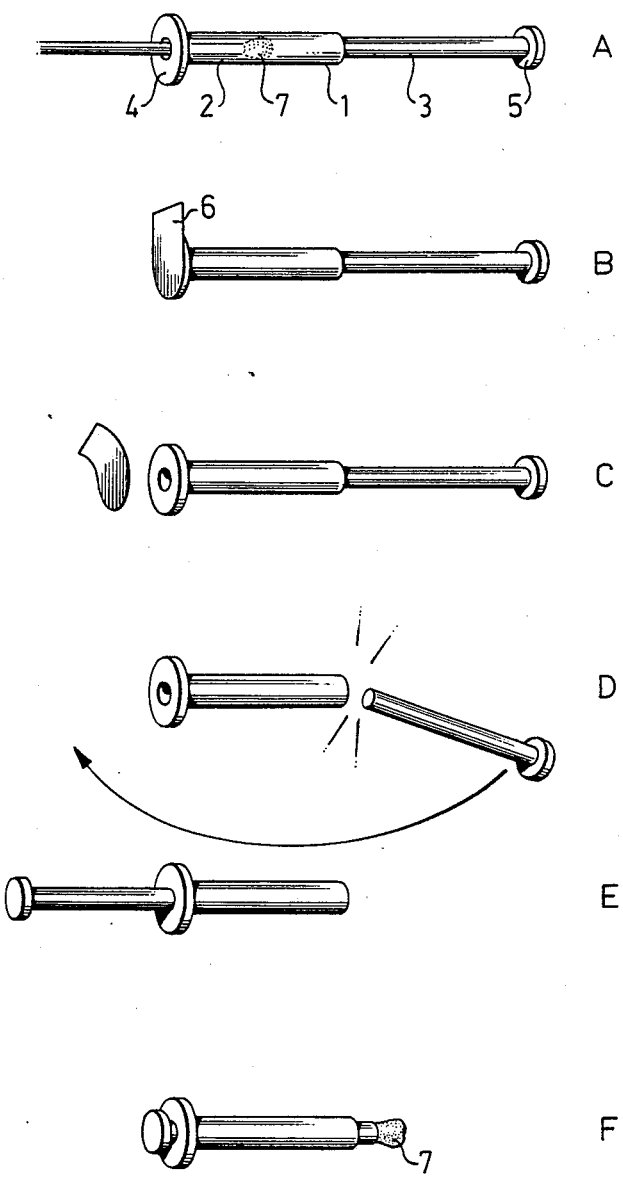
FIG. 1, views A–F, discloses an applicator and, the principle of operation of an applicator of the invention.

FIG. 1 shows an applicator of the invention which comprises an elongated body 1 including two sections 2 and 3. The tubular section comprising the medicament reservoir 2 is sealed at one end by a second rod-like section which is designed to serve as a plunger 3. A grip 5 (not necessary) is provided at the other end of the plunger 3. At the other end of the reservoir 2, the end opening which is not sealed by the plunger 3, there is preferably provided a flange 4 which provides a larger surface for affixing a sealing means 6, which for instance may take the form of an adhesive tape. In view A of FIG. 1, a substance or medicament 7 is filled into the reservoir 2. The method for filling (A), sealing (B), opening both ends of the reservoir 2 (C and D), introducing the plunger 3 into the reservoir 2 (D and E) and ejecting the substance or medicament 7 from the reservoir 2 (F) is disclosed in the sequence of views A–F of FIG. 1.

Figure 2:
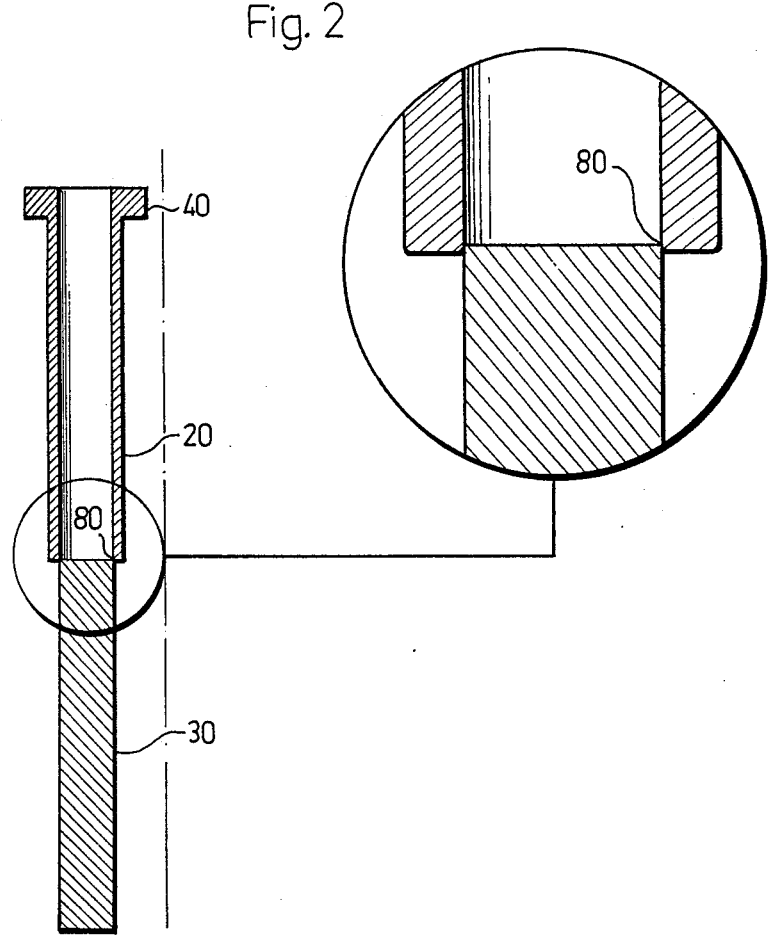
FIG. 2 is a sectional view of an applicator of the invention.

FIG. 2 shows an applicator which is ready for filling. The elongated body comprises the medicament reservoir barrel 20 and a plunger 30 sealing one opening of the reservoir 20. This figure also shows the breakable integral joint or contact surface at 80.

The elongated body of the applicator is preferably made of a molded plastic by techniques well known in the art. Suitable manufacturing processes include both injection molding and blow molding.

The material thickness at the breaking joint 80 varies depending on the polymer material used, the manufacturing process and the intended use of the final product. For the applicator embodiment illustrated in FIG. 2 it could for example be 0.1 mm. The breakable contact surface should be such that the plunger 30 is firmly joined to the reservoir 20 yet still may be comfortably broken off or detached. The configuration of the breakable contact surface can vary and is determined by the shape of the form which is used for the moulding process, as will be obvious to one of ordinary skill in the art. The applicator disclosed in FIG. 2 can be easily and inexpensively manufactured by injection moulding.

A special advantage inherent to the embodiment of the invention disclosed in FIGS. 1 and 2 concerns the hygiene aspect, explained as follows. The end of the plunger 3 which upon insertion into reservoir 2 becomes the leading end is adjacent to and seals the reservoir opening. When the applicator is readied for use the plunger 3 is broken off from the reservoir immediately before use and the leading end (as defined above) of plunger 3 is inserted into the reservoir in order to remove the medicine contained therein. By using the applicator in this way the risk of contaminating the medicament is minimal.

FIGS. 3, 4 and 5 show the principle for an applicator manufactured by a blow moulding technique. In FIGS. 3 and 4, the medicament reservoir 200 and the plunger 300 are integrally joined at C. A is the inner diameter of the reservoir 200 and the outer diameter of the plunger 300 which is insertable into the reservoir 200 as disclosed in FIG. 5. B indicates the length of the plunger 300 and the length of the medicament reservoir 200.

In FIG. 3, the medicament can be filled into the reservoir 200 through the means 900 which constitutes a sealing means 600 when pressed together as illustrated in FIG. 4.

In FIG. 5, the sealing means 600 as well as the plunger 300 have been broken off and plunger 300 introduced into the medicament reservoir 200.

As stated above, FIGS. 3, 4 and 5 disclose a principle for an applicator made by a blow moulding technique. If the applicator is to be used for large volumes and/or relatively low viscosity liquids (solutions) auxiliary means known to the man skilled in the art must be provided.

According to a preferred embodiment of the invention the shape of at least the leading end of the plunger is essentially the same as or congruent to the shape of the inside of the reservoir, and the largest cross sectional dimensions of the plunger are only slightly smaller than the cross sectional inner dimensions of the reservoir. It is also preferred that the cross sectional dimensions of the plunger and of the outside and inside of the reservoir are relatively uniform.

According to a preferred embodiment essentially the whole rod-like plunger section is inserted into the reservoir and the shape of the exterior surface of the plunger is substantially congruent to or the same as the shape of the interior surface of the barrel reservoir section. Optionally, a grip may be provided at or near one end of the plunger. The length of the plunger (the grip not being included) should be essentially the same as the outer length of the reservoir. Alternatively, the plunger could be slightly longer than the outer length of the reservoir. In both cases the length of the plunger inserted into the reservoir should be sufficient to ensure complete ejection of all the medicament from the reservoir when the plunger is fully introduced into the length of the reservoir.

According to another embodiment of the invention, the plunger is essentially longer than the medicament reservoir and in this case there is provided a means on the plunger which stops the sliding movement of the plunger at a predetermined distance from the leading end of the plunger. This distance corresponds essentially to the outer length of the reservoir in order to ensure complete removal of the medicament from the reservoir when the plunger is inserted. The part of the plunger behind the stopping means may then serve as a handle. As one of ordinary skill in the art will appreciate from this disclosure, grooves or recesses may be provided behind the leading end of the rod-like plunger section in order to save material and reduce manufacturing cost. Another way of saving material is to make the plunger itself hollow, e.g. in the form of a hollow cylinder. The plunger section may also be designed to have a leading end fitting slidably and exactly to the inside of the reservoir which is affixed to an elongated rod having smaller cross sectional dimensions. It is preferred that the plunger as well as the inside and outside of the reservoir are cylindrically shaped.

According to another embodiment, the plunger and the inside of the reservoir are slightly tapered and the opening of the leading end of the applicator, i.e. the end to be inserted into the body cavity, is slightly smaller than the opposite opening of the reservoir. Such an applicator is illustrated by FIGS. 3–5.

The opening of the reservoir section, which in the elongated applicator body is sealed by integral joining with the plunger section, could have essentially the same cross sectional dimensions as the cross sectional dimensions of the inside of the reservoir. This means that when the plunger section is broken off from the barrel section of the elongated body, which constitutes the medicament reservoir, a relatively large, preferably circular, hole is obtained. A large hole may be preferred when the medicament in the reservoir is a solid substance, e.g. a suppository, or when the medicament is present in the form of a liquid of high viscosity such as a gel or an ointment. In this context, it should be mentioned that although the applicator according to the invention can be used for administering different kinds of medical compositions such as solutions, ointments, gels, suppositories, vagitories, into different body cavities such as the nose, rectum, vagina, a preferred embodiment concerns an applicator for administering high viscosity liquids or gels including an active substance into the nose.

The active substance may be any substance within human or veterinary medicine which is suitable for nasal administration. Although the applicator according to the invention is preferred for administering medicines to humans and animals, it is apparent that it can also be used within other fields, e.g. within the cosmetic and food industry, for any substance which requires application to any area or surface.

When the reservoir is prefilled with a liquid of low viscosity it is preferred that the opening provided in the reservoir from which the medicament will be ejected be smaller than the cross sectional diameter of the reservoir in order to avoid a too rapid administration of the drug. One way of achieving a relatively small hole in the leading end of the applicator reservoir is to make the leading end tapered.

In order to ensure complete removal of the medicament from the reservoir the leading end of the plunger section should be shaped correspondingly. Instead of manufacturing the reservoir so that only one hole is obtained when the plunger is broken off the applicator can be manufactured in such a way that a plurality of smaller holes are provided and "opened" for passage of the medicament when the plunger section is broken off. Furthermore, if desired there could also be provided holes in the cylindrical wall of the reservoir.

The other end of the medicament reservoir can be sealed by any conventional sealing means such as a cap, a plug, an adhesive tape, etc.

Although the invention has been disclosed and described with reference to its preferred embodiments, one of ordinary skill in the art may appreciate modifications and changes which may be incorporated therein that do not depart from the scope and spirit of this invention as described above or claimed hereafter.

We claim:

1. A body for a disposable syringe type substance applicator, comprising:
    a body having a hollow barrel section and a plunger section, said body being initially a single piece,
    said hollow barrel section having one end sealed by integrally joining thereto said plunger section which is separable to unseal said barrel end by breaking of the integral joint, one end portion of said plunger section for insertion into said barrel section, said one end portion being closed, having an exterior surface shape substantially congruent to a portion of the interior surface of said barrel section and sized to be slidable within the entire length of said barrel section.

2. The body of claim 1, wherein the cross sectional dimensions of said plunger end portion is only slightly smaller than the corresponding dimensions of the interior cross section of said barrel element.

3. The body of claim 2, wherein said barrel and plunger sections are of circular cross section.

4. The body of claim 2, wherein the exterior surface of said plunger section and the interior shape of said barrel section are cylindrical.

5. The body of claim 1, wherein said plunger section is essentially as long as said barrel section.

6. The body of claim 1, wherein the end portion of said plunger section which is integrally joined to said sealed end of said barrel section is the end portion of said plunger section which has an exterior surface shape substantially congruent shape to the interior surface of said barrel section and is the end portion for insertion into said barrel section.

7. The body of claim 1, wherein said integrally joined barrel and plunger sections are made by injection molding of a polymer.

8. The body of claim 1, wherein said integrally joined barrel and plunger sections are made by blow molding of a polymer.

9. The body of claim 1, wherein said plunger section has essentially the same shape as the outside of said barrel section.

10. A disposable, single dose substance applicator, comprising:
    an elongated body having a hollow barrel section and a plunger section, said body being initially a single piece, said hollow barrel section having two end openings, one end opening of which is sealed by integrally joining thereto said plunger section which is separable to unseal said barrel end opening by breaking of the integral joint, one end portion of said plunger section for insertion into said barrel section, said one end portion being closed, having an exterior surface shape substantially congruent to a portion of the interior surface of said barrel section and sized to be slidable within the entire length of said barrel section; and
    a detachable sealing means engaged about said other end opening of said barrel section.

11. The applicator of clai 10, further comprising a substance for application deposited within said barrel section.

12. The applicator of claim 11, wherein said substance is a medicament.

13. The applicator of claim 12, wherein the cross sectional dimensions of said plunger end portion are only slightly smaller than the corresponding dimensions of the interior cross section of said barrel element.

14. The applicator of claim 13, wherein said barrel and plunger sections are of circular cross section.

15. The applicator of claim 13, wherein the exterior surface of said plunger section and the interior surface of said barrel section are cylindrical.

16. The applicator of claim 12, wherein said plunger section is essentially as long as said barrel section.

17. The applicator of claim 12, wherein the end portion of said plunger section which is integrally joined to said one end opening of said barrel section is the end portion of said plunger section which has an exterior surface shape substantially congruent shape to the interior surface of said barrel section and is the end portion for insertion into said barrel section.

18. The applicator of claim 12, wherein said integrally joined barrel and plunger sections are made by injection molding of a polymer.

19. The applicator of claim 12, wherein said integrally joined barrel and plunger sections are made by blow molding.

20. The applicator of claim 12, wherein said medicament is a high viscosity liquid for nasal administration.

* * * * *

UNITED STATES PATENT AND TRADEMARK OFFICE
CERTIFICATE OF CORRECTION

PATENT NO. : 4,900,315

DATED : February 13, 1990

INVENTOR(S) : Lundquist, et al.

It is certified that error appears in the above-identified patent and that said Letters Patent is hereby corrected as shown below:

Col. 1, between lines 65 and 66 insert --Summary of the Invention--

At col. 1, lines 66-67, please delete --of the Invention--.

At col. 2, line 25, following the word "and" please delete the --,--.

At col. 2, line 36, please change "EMBODIMENT" to --EMBODIMENTS--.

At claim 11, line 27, please change "clai" to --claim--.

Signed and Sealed this

Twenty-sixth Day of February, 1991

Attest:

HARRY F. MANBECK, JR.

*Attesting Officer*     *Commissioner of Patents and Trademarks*